United States Patent [19]
Allewalt

[11] Patent Number: 5,619,750
[45] Date of Patent: Apr. 15, 1997

[54] EYES-EARS-NOSE PROTECTOR

[76] Inventor: Donald L. Allewalt, 8 Rainflower Path No. 103, Sparks, Md. 21152

[21] Appl. No.: 567,134

[22] Filed: Dec. 4, 1995

[51] Int. Cl.⁶ .................... A61F 9/00; G02C 5/14
[52] U.S. Cl. .................... 2/13; 2/449; 351/123
[58] Field of Search .................... 2/13, 209, 12, 2/15, 9, 449, 10, 423; 351/158, 155, 131, 132, 138, 123, 122, 47, 44, 156

[56] References Cited

U.S. PATENT DOCUMENTS

| | | | |
|---|---|---|---|
| 1,048,191 | 12/1912 | Maurice | 2/13 |
| 1,117,968 | 11/1914 | De Bobory | 2/14 |
| 1,468,556 | 9/1923 | Camp et al. | |
| 1,621,629 | 3/1927 | Dawson | 2/209 |
| 2,197,973 | 4/1940 | Everett et al. | 2/13 |
| 2,403,223 | 7/1946 | Kaesz | 2/13 |
| 3,346,875 | 10/1967 | Weisberger | 2/9 |
| 3,436,761 | 4/1969 | Liautaud et al. | 2/13 |
| 3,721,490 | 3/1973 | Prince | 351/47 |
| 4,670,911 | 6/1987 | Dunford | 2/209 |
| 4,682,374 | 7/1987 | Geiser | 2/449 |
| 4,751,746 | 6/1988 | Rustin | 2/13 |
| 4,786,159 | 11/1988 | Piazza, Sr. et al. | 351/158 |
| 5,086,789 | 2/1992 | Tichy | 2/209 |
| 5,092,667 | 3/1992 | Bagley | 351/123 |
| 5,167,036 | 12/1992 | Daprato | 2/2 |
| 5,201,856 | 4/1993 | Edwards | 2/209 |
| 5,323,493 | 6/1994 | Ogiba | 2/422 |
| 5,416,923 | 5/1995 | Peugh | 2/9 |
| 5,438,706 | 8/1995 | Lambur | 2/13 |

FOREIGN PATENT DOCUMENTS 356552  9/1931  United Kingdom .............. 2/209

*Primary Examiner*—Amy B. Vanatta
*Attorney, Agent, or Firm*—Leonard Bloom

[57] ABSTRACT

An eyes-ears-nose protector includes eye-glasses with attached nose shield, side shields and ear shields to protect simultaneously the nose, eyes, and ears from direct and side excessive sunlight.

9 Claims, 10 Drawing Sheets

EYES-EARS-NOSE PROTECTOR

BACKGROUND OF THE INVENTION

The present invention relates to a safety equipment allowing a simultaneous protection of a wearer's eyes, ears and nose from environmental influence, particularly, from sunlight.

It is known that people living or travelling in hot localities, are subjected to a considerable amount of sunlight, which may cause burning of skin on the nose and ears, produces vision inconvenience, and sometimes also causes serious eye problems.

There were certain attempts undertaken in the field to provide these people with sunshields for different parts of the body. For example, a sunshield for the nose, was described in U.S. Pat. Nos. 1,048,191; 2,197,973; and 5,167,036. The shield is secured to a pair of eyeglasses and is formed either as to practically follow the configuration of the nose, extends outward above the nose with or without engaging the nose, or covers the upper surface of the nose.

A nose and lip protector, described in U.S. Pat. No. 3,346,875, is detachably connected to a pair of eyeglasses.

U.S. Pat. Nos. 1,621,629 and 4,757,746 describe ear protectors attached to eyeglasses. For instance, U.S. Pat. No. 4,757,746 describes a protector, preferably for skiers, which can be readily mounted on a temple of glasses and extends from the front of the glasses to and beyond the ear piece of the temple so that there will be protection against wind and sun for a wearer's eyes, the side of the face and ears. The protector is formed of a cloth having insulating characteristics.

To provide a side protection for eyes, the U.S. Pat. No. 3,721,491 describes a removable clear side shield slidably mounted on the eyeglasses temple.

Although the above-referenced inventions provide a sun protection for one or two parts of the body, none of them can provide sun protection to eyes, nose and ears altogether simultaneously.

BRIEF SUMMARY OF THE INVENTION

It is, therefore, an object of the present invention to provide a simple and lightweight protector for shielding simultaneously eyes, ears and nose of a wearer against the undesirable sunlight.

The present invention finds its particular utility as a means for sunlight protection for people subjected to extensive sunlight.

In accordance with the teaching of the present invention, an eyes-ears-nose protector includes eyeglasses having a pair of lenses and a pair of temple bars. A nose shield is attached to the eyeglasses between the lenses, a pair of side shields is immovably attached to the eyeglasses and is angled in respect to the lenses, and an ear shield is immovably attached to an ear end of each temple bar. When the wearer puts the protector on, the upper surface of a nose is covered by the nose shield, the top of each ear is covered by the ear shield, and the eyes are protected by the lenses and the side shields from the direct and side sunlight.

The ear shield is an integral member preferably comprising first, second and third surfaces. One edge of the integral member is curved to substantially follow a shape of the ear end of the temple bar. This curved edge is immovably connected to the ear end of the temple bar. The second surface of the integral unit is angled outwardly from the first surface, and the third surface is tilted outwardly and down from the second surface, such that the second and third surfaces, in combination, cover the top of the ear.

A frame of the eyeglasses embraces and holds the lenses and the side shields. The frame has a front portion holding the pair of lenses, and a pair of side portions, each holding a respective side shield. The side shields are tilted in respect to the lenses to conveniently embrace the face of the wearer. Each temple bar is pivotally connected to a respective side portion of the frame. The lenses and the side shields are made of a semi-opaque material blocking excessive sunlight.

These and other objects of the present invention will become apparent from a reading of the following specification taken in conjunction with the enclosed drawings.

DESCRIPTION

Referring to FIGS. 1–12, an eyes-ears-nose protector (further, protector) 10 is intended to simultaneously protect the nose, eyes and ears of a person from a damaging influence of excessive sunlight.

Figure 1:
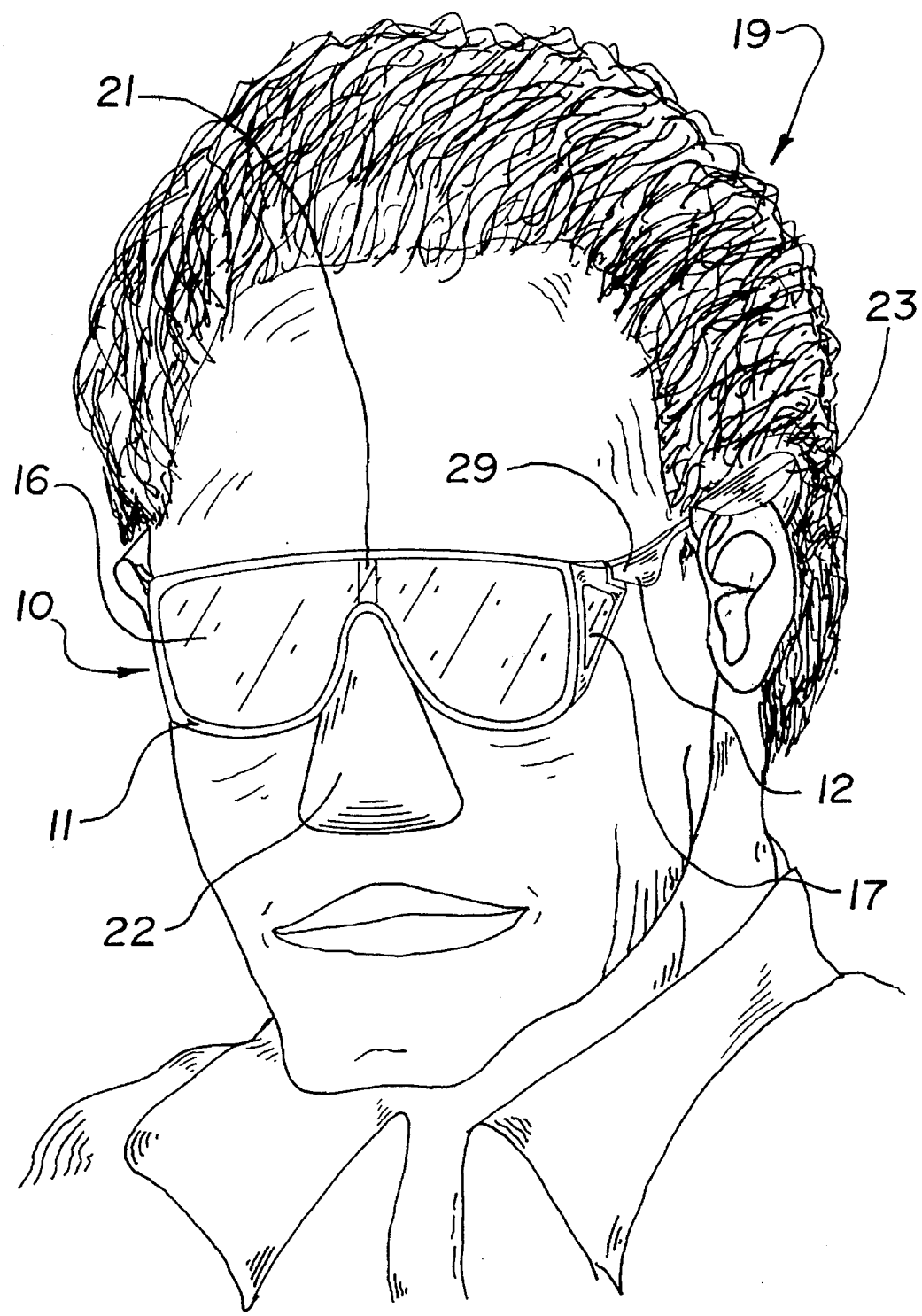
FIG. 1 is a perspective view of the eyes-ears-nose protector of the present invention as worn by an individual.

The protector 10 comprises a frame 11 and a pair of temple bars 12 pivotally connected to sides 13 and 14 of the frame 11. The frame 11 includes a front portion 15 integrally connecting sides 13 and 14. The front portion 15 holds lenses 16, while sides 13 and 14 hold side shields 17 and 18. The lenses 16 may include a pair of lenses, or may be formed as a single lens shield (as best shown in FIG. 1).

The lenses (or the single lens shield) 16, similar to the side shields 17 and 18, are made of a semi-opaque material which blocks the excessive sunlight from penetrating through this material, but which allows the person wearing the protector 10 to see through the lenses 16. As best shown in FIGS. 1–7, the front portion 15 holds lenses 16 to protect the person from direct frontal sunlight, while the side shields 17, 18 protect the person from side sunlight. The sides 13, 14 are angled in respect to the front portion 15, so as to conveniently follow the contour of the face of the person-wearer 19, and the lenses 16 and side shields 17, 18 are immovably held by the frame 11.

Figure 2:
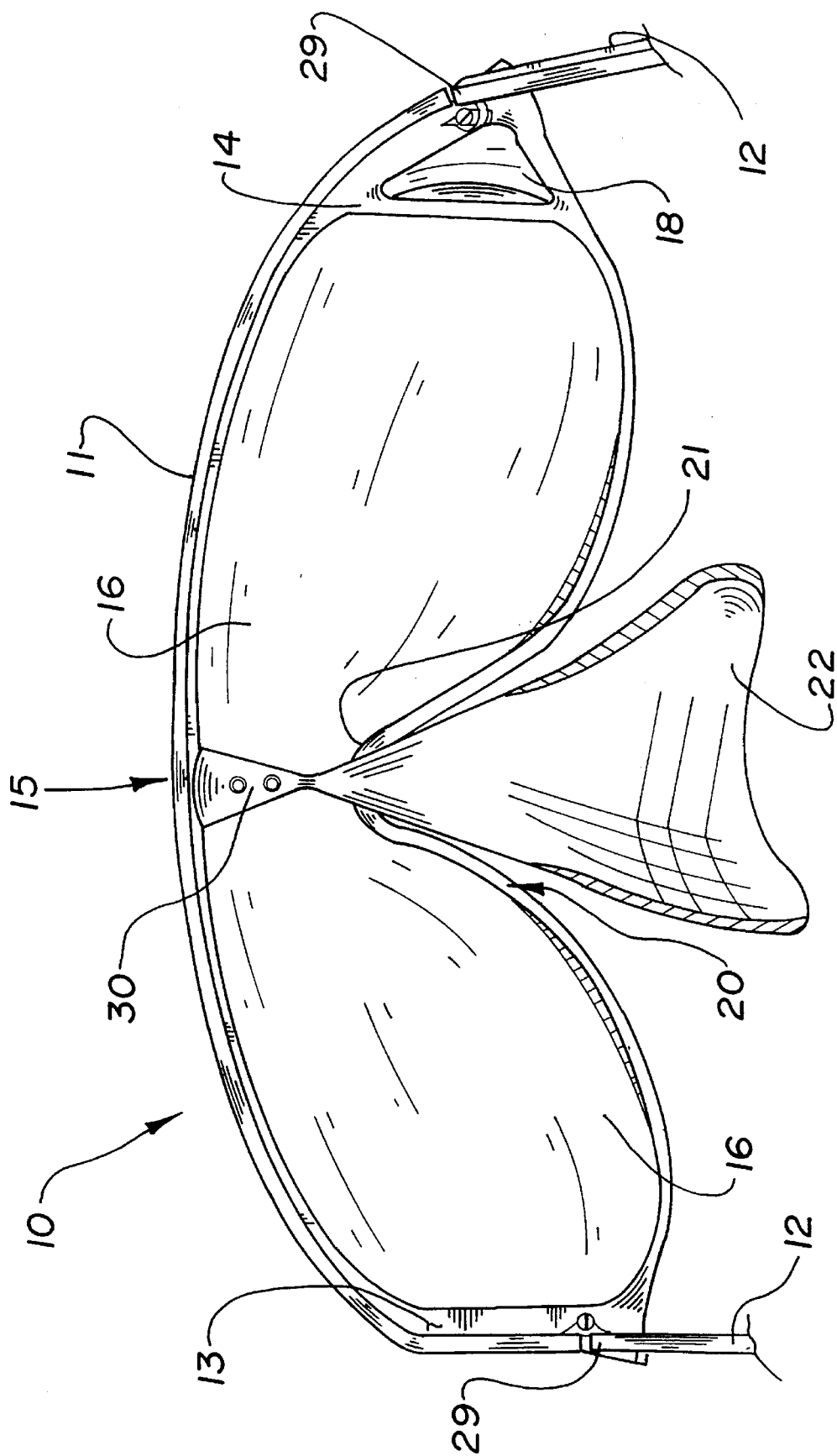
FIG. 2 is a view of the protector from inside showing the nose shield attached by means of a living hinge.
Figure 3:
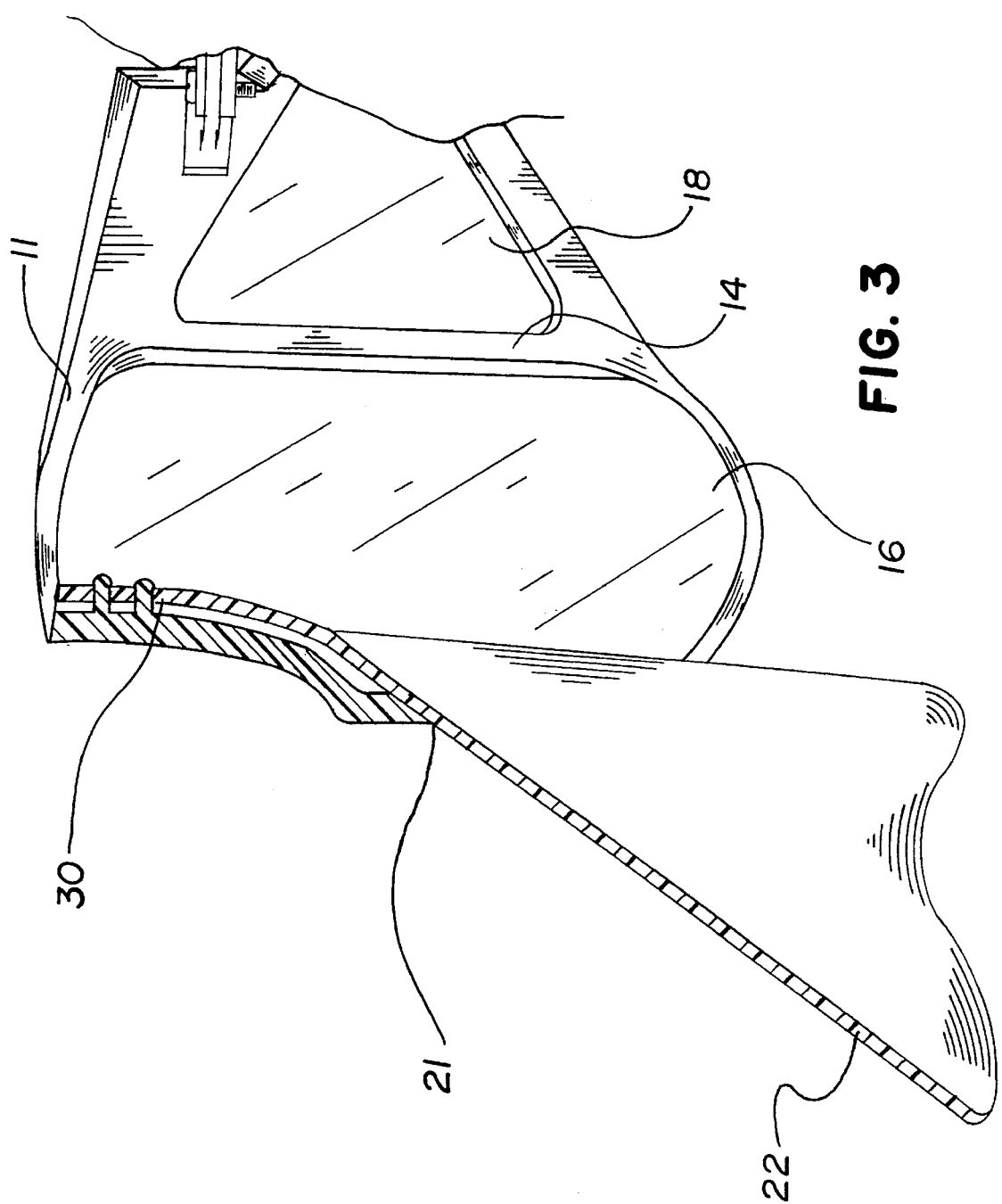
FIG. 3 is a longitudinal cross-section of the protector of FIG. 2.
Figure 4:
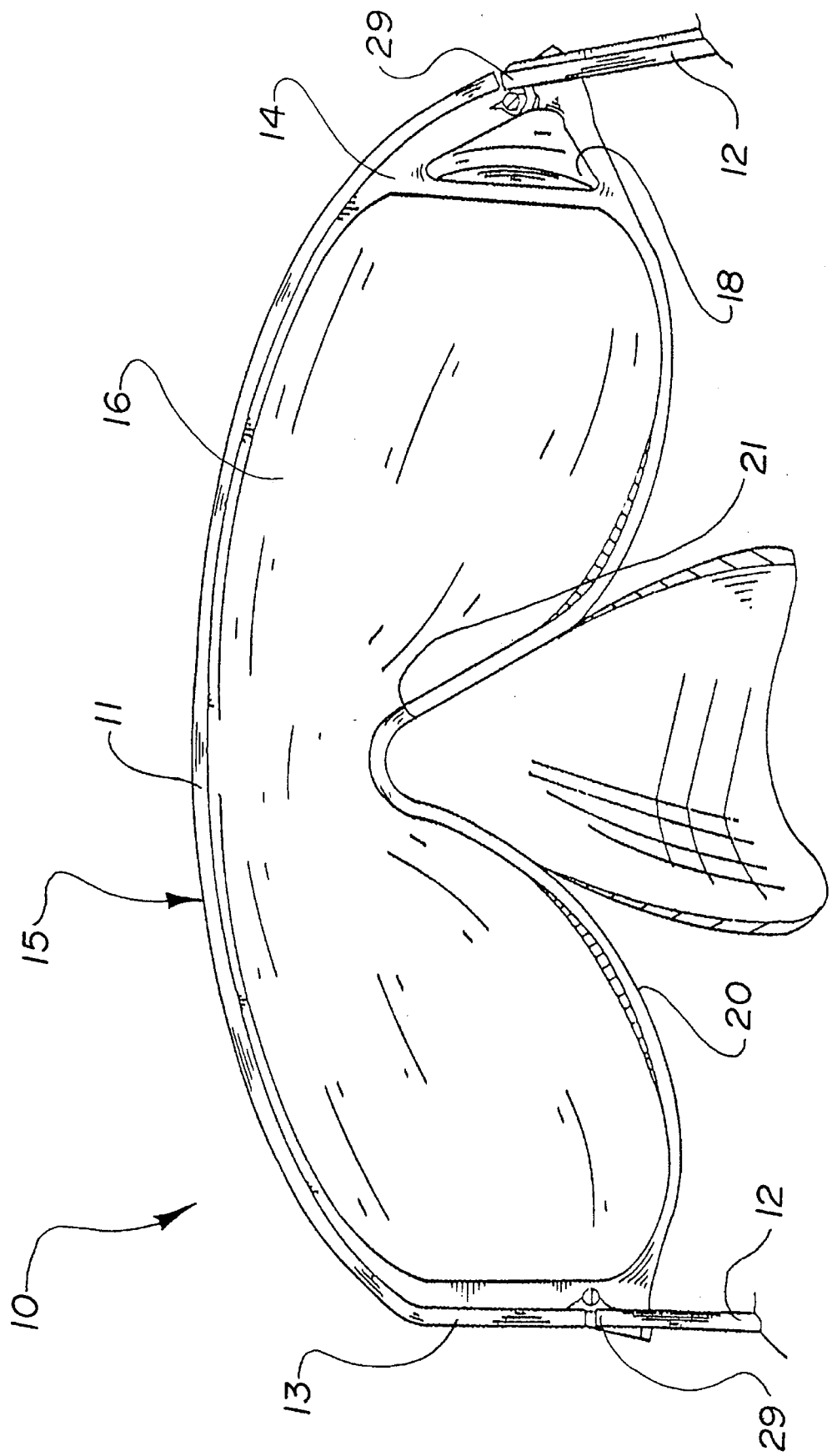
FIG. 4 is a view of the protector from inside showing the nose shield molded to the frame.
Figure 5:
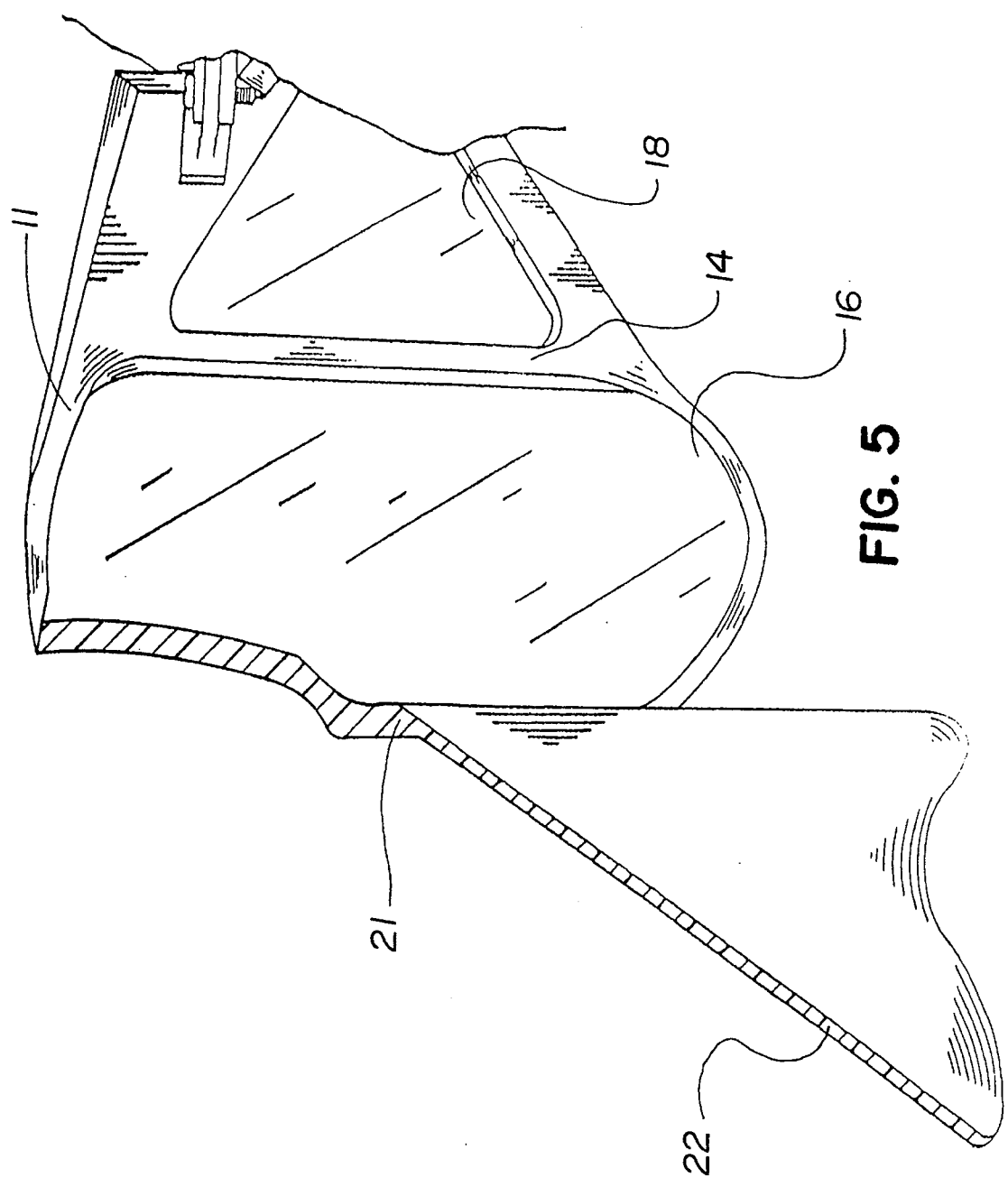
FIG. 5 is a longitudinal cross-section view of the protector of FIG. 4.

The front portion 15 of the frame 11 is curved in its lower part 20 to form a nose engaging area 21 engaging the nose of the person 19 when the protector 10 is put on. A nose shield 22 (best shown in FIGS. 1–7) is attached (integrally or removably) to the nose engaging area 21 to cover the upper surface of the nose. The nose shield 22 can be attached by means of a living hinge 30 (as best shown in FIGS. 2, 3), or can be molded with the frame 11 (as best shown in FIGS. 4, 5) or by other means known to those skilled in the art.

A pair of ear shields 23 shown in FIGS. 1, 6–12, are immovably secured to ear ends 24 of the temple bars 12. Each ear end 24 is curved to be conveniently held by the ears of the person 19. The ear shield 23 is an integral member which has three surfaces 25, 26, 27. The edge 28 of the surface 25 is curved to substantially follow the shape of the ear end 24 to which this edge 28 is connected such that the ear shield 23 is immovably connected to the respective temple bar 12.

The nose shield 22 and the ear shields 23 can be made of any material utilized for blocking the excessive sunlight, and preferably of the same material as the side shields 17 and 18.

Preferably, the ear shield 23 and the temple bar 12 is an integrally molded plastic piece. The surface 26 is angled outwardly from the surface 25, and the surface 27 in tilted outwardly and down from the surface 26, such that both surfaces 25 and 26 combine to cover the top of the ear, thereby shielding it from burning by the sun-radiation, as best shown in FIGS. 1 and 8.

Figure 6:
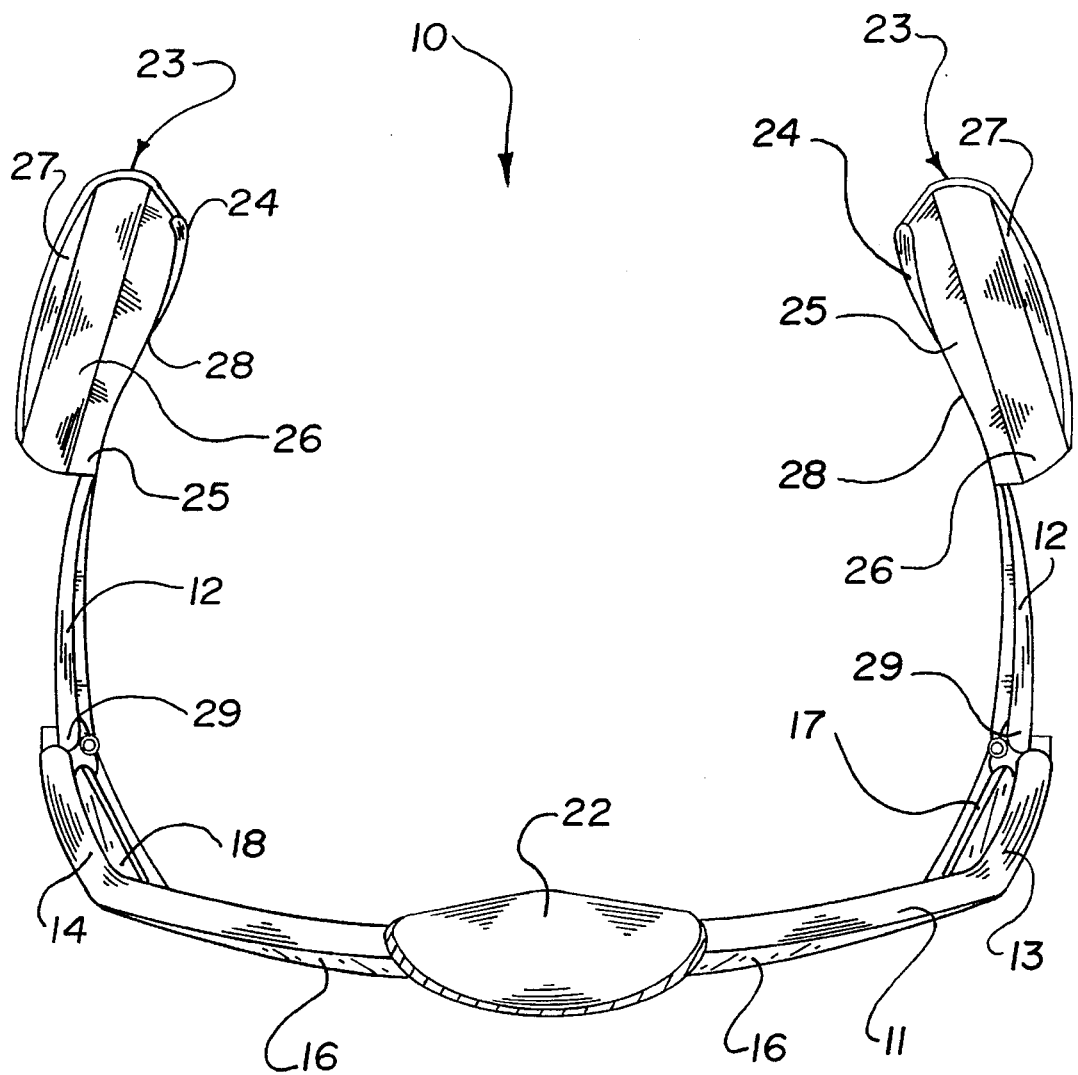
FIG. 6 is a top elevational view of the protector.
Figure 7:
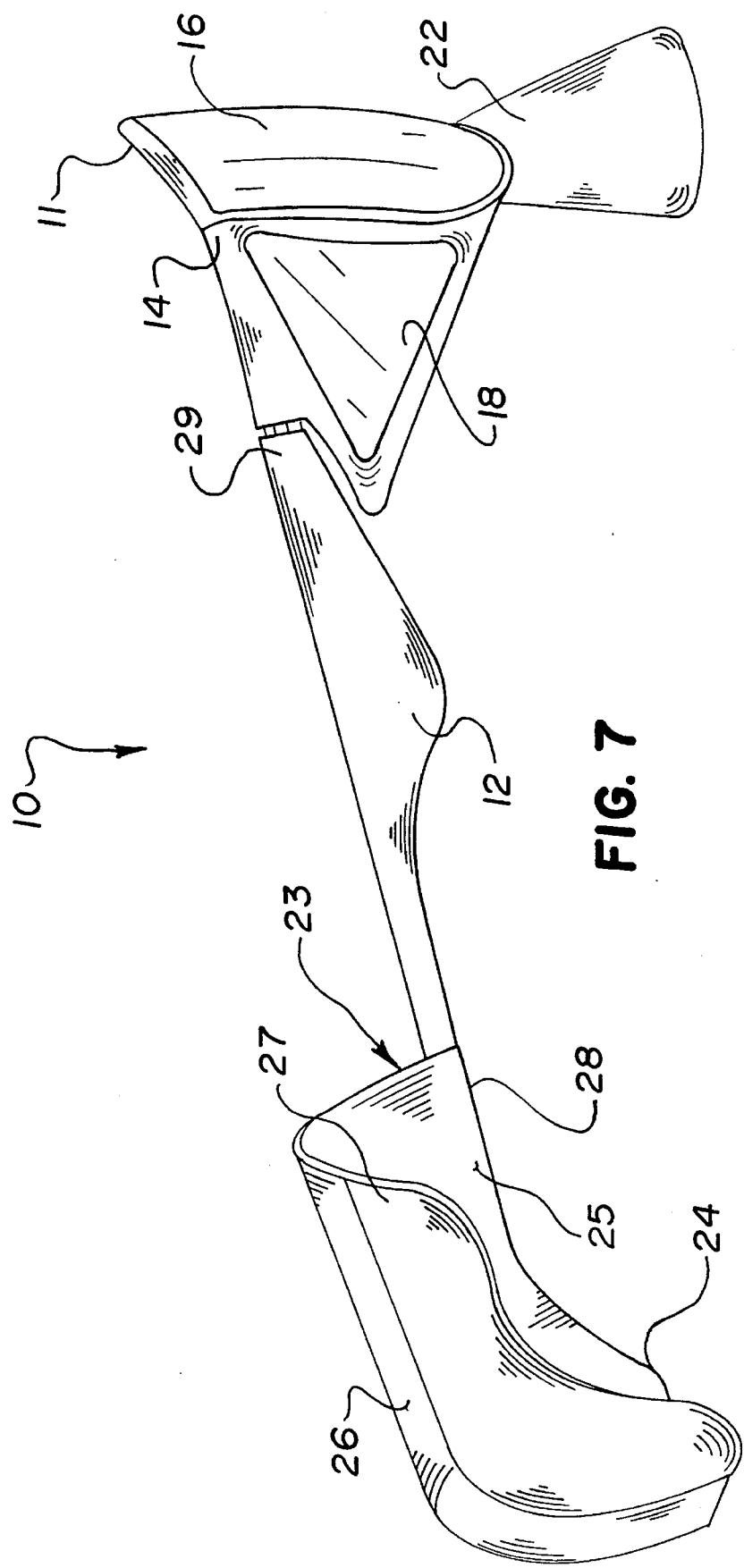
FIG. 7 is a side view of the protector.
Figure 8:
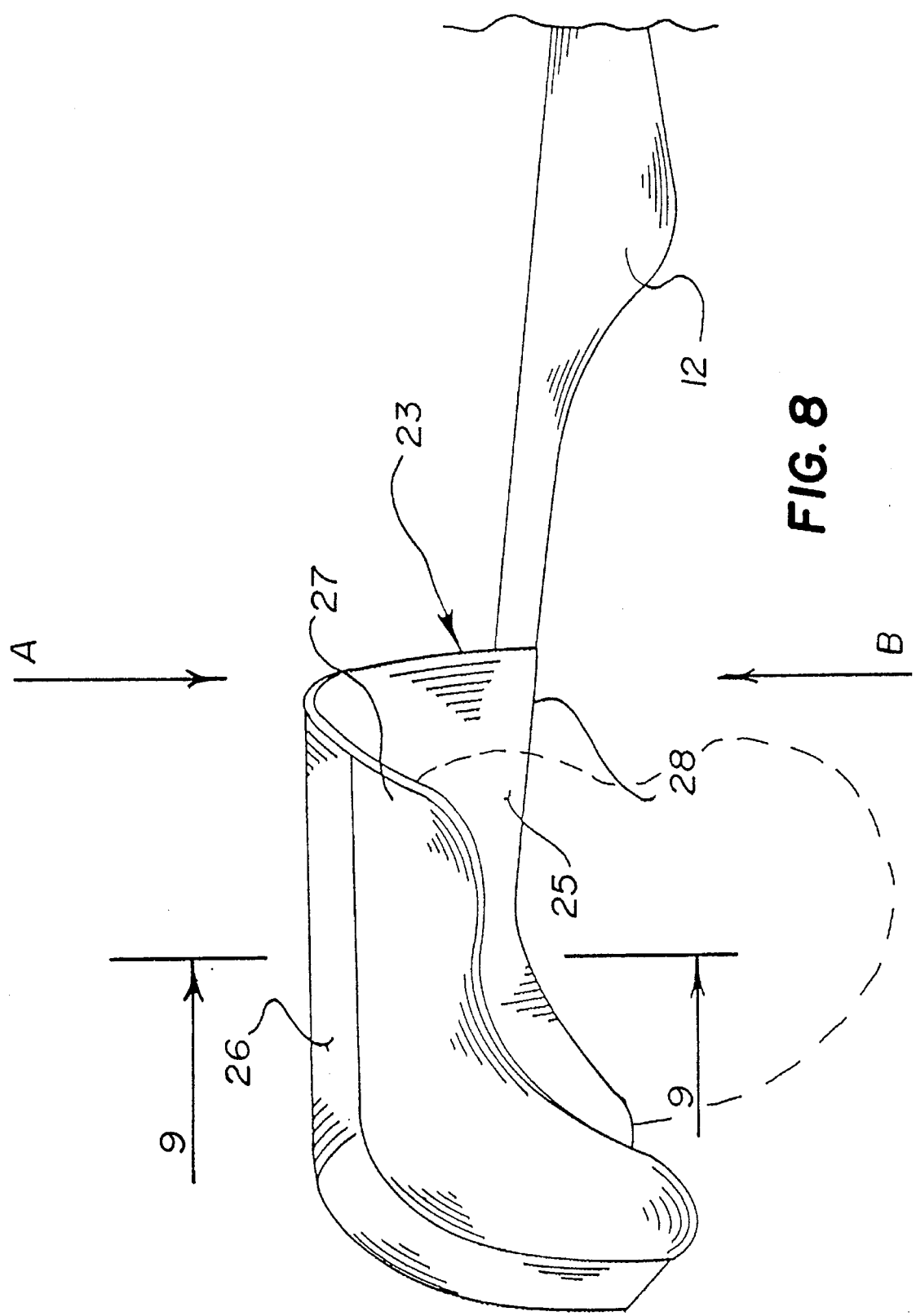
FIG. 8 is a partial view of the protector showing the ear shield in enlarged scale.
Figure 9:
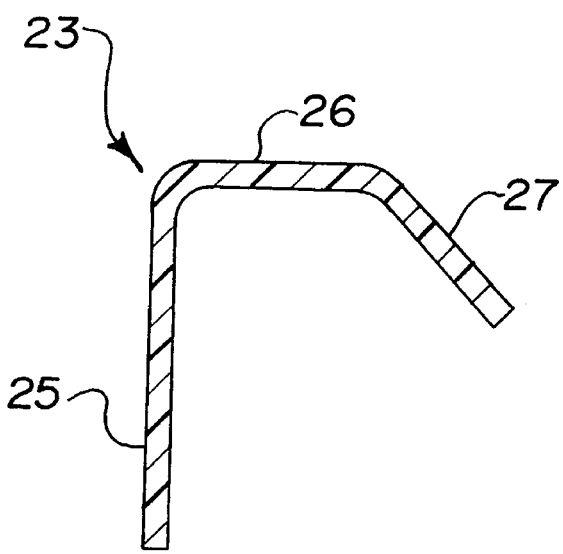
FIG. 9 is a cross-section of the ear shield of FIG. 8 taken along lines 9—9.
Figure 10:
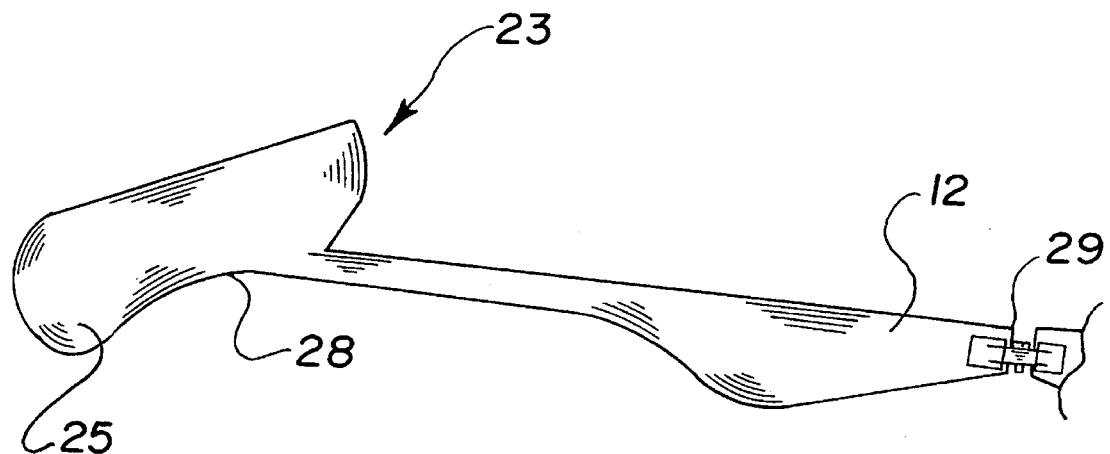
FIG. 10 is a side view of the ear shield.
Figure 11:
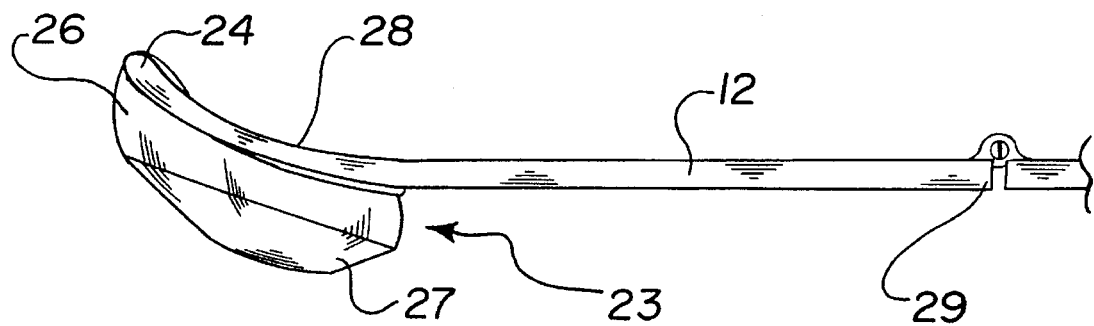
FIG. 11 is a view of the temple bar seen in A direction of FIG. 8.
Figure 12:
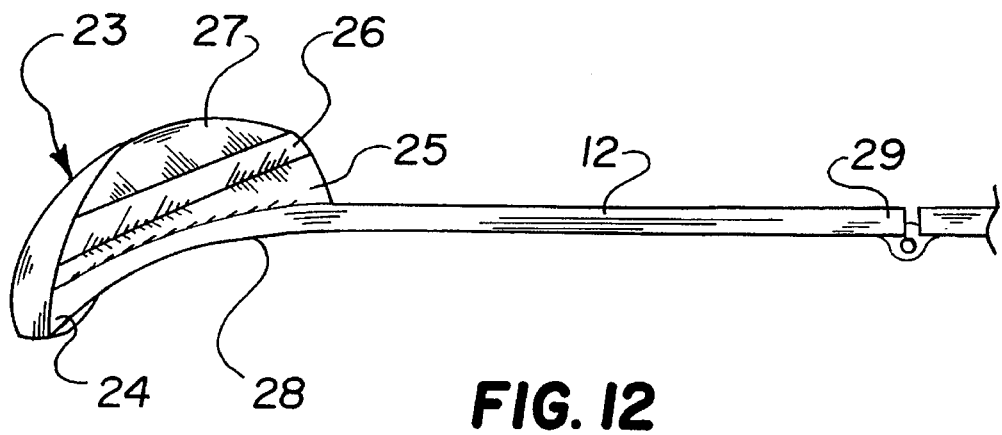
FIG. 12 is a view of the temple bar seen in B direction of FIG. 8.

As best shown in FIGS. 6, 8, and 10, the end 29 of the temple bar 12 is pivotally secured to a respective side 13, 14 of the frame 11.

Obviously, many modifications may be made without departing from the basic spirit of the present invention. Accordingly, it will be appreciated by those skilled in the art that within the scope of the appended claims, the invention may be practiced other than has been specifically described herein.

I claim:

1. A protector preventing a wearer's eyes, ears and nose from being injured by an excessive sunlight, the protector comprising:

eye-glasses having lenses and a pair of temple bars, each temple bar having an ear end;

a nose shield attached to the eyeglasses;

a pair of side shields, each immovably attached to a respective side of the eyeglasses and angled in respect to said lenses; and a pair of ear shields, each immovably attached to the ear end of a respective temple bar;

wherein, when the wearer puts said protector on, an upper surface of the nose is covered by the nose shield, a top of each ear is covered by the ear shield, and the eyes are protected by the lenses and the side shields from direct and side sunlight.

2. The protector of claim 1, wherein the ear end of the temple bar is curved to be conveniently held by an ear, wherein the ear shield is an integral member comprising first, second and third surfaces, wherein one edge of the integral member is curved to substantially follow a shape of the ear end of the temple bar, said one edge being immovably connected to said ear end of the temple bar, wherein the second surface is angled outwardly from the first surface, and wherein the third surface is tilted outwardly and down from the second surface, such that the second and the third surfaces, in combination, cover the top of the ear.

3. The protector of claim 1, further comprising a frame having a front portion holding said lenses, and a pair of side portions, each holding a respective side shield, wherein said side shields are tilted in respect to said lenses to conveniently follow the contour of the face of the wearer, and wherein each temple bar is pivotally connected to a respective side portion of the frame.

4. The protector of claim 1, wherein the lenses and the side shields are made of a semi-opaque material blocking excessive sunlight.

5. A sunlight protector comprising:

eyeglasses having a lens shield;

a pair of temple bars, each temple bar having an ear end; and a pair of ear shields, each immovably attached to the ear end of a respective temple bar, wherein the ear end of each of said pair of temple bars is curved to be conveniently held by an ear;

wherein each of said pair of ear shields is an integral member comprising first, second and third surfaces;

wherein one edge of the first surface is curved to substantially follow a shape of the ear end, said one edge being immovably connected to said ear end;

wherein said second surface is angled outwardly from the first surface, and said third surface is tilted outwardly and down from the second surface, such that the second and the third surfaces, in combination, cover a top of the ear, thereby protecting the top of the ear from an excessive sunlight.

6. The sunlight protector of claim 5, further including a pair of side shields, each immovably attached to a respective side of the eyeglasses, and angled in respect to said lens shield, wherein said lens shield and said pair of side shields protect eyes from a direct and side excessive sunlight.

7. The sunlight protector of claim 6, wherein the lens shield and each of said pair of side shields is made of a semi-opaque material blocking the excessive sunlight.

8. The sunlight protector of claim 5, wherein the eyeglasses further includes a frame having a front portion holding said lens shield, said front portion includes a nose engaging area and wherein a nose shield is attached to said nose engaging area to cover an upper surface of a nose.

9. The sunlight protector of claim 5, wherein said each of the pair of ear shields is molded integrally with said respective temple bar.

\* \* \* \* \*